United States Patent [19]

Kimura et al.

[11] Patent Number: 4,596,775
[45] Date of Patent: Jun. 24, 1986

[54] MICROORGANISM AND ITS USE FOR THE PREPARATION OF GLUTATHIONE

[76] Inventors: Akira Kimura, 80-2, Wakamiya-dori 6-jo-agaru, Kami-wakamiya-cho, Shimogyo-ku, Kyoto-shi, Kyoto-fu; Kousaku Murata, 3-35, Nishino Hitsugawa-cho, Yamashina-ku, Kyoto-shi, Kyoto-fu; Jyoji Kato, 25-16, Otokoyama Yoshii, Yawata-shi, Kyoto-fu, all of Japan

[21] Appl. No.: 670,675

[22] Filed: Nov. 13, 1984

Related U.S. Application Data

[63] Continuation of Ser. No. 402,698, Jul. 28, 1982, abandoned.

[30] Foreign Application Priority Data

Jul. 30, 1981 [JP]  Japan ................................ 56-120544
Jul. 30, 1981 [JP]  Japan ................................ 56-120545

[51] Int. Cl.$^4$ ...................... C12P 21/02; C12N 11/18; C12N 1/20; C12N 15/00
[52] U.S. Cl. ....................................... 435/70; 435/175; 435/253; 435/172.1; 435/849
[58] Field of Search ................. 435/70, 128, 183, 848, 435/849, 175, 106, 253, 172.1

[56] References Cited

FOREIGN PATENT DOCUMENTS 82099   7/1981   Japan ..................................... 435/70

OTHER PUBLICATIONS

Murata et al., J. Gen. Microbiol., 120(2): 545–547 (1980).
Murata et al., Chemical Abstracts, 92: 159663q, p. 233 (1980).

Primary Examiner—Esther M. Kepplinger
Attorney, Agent, or Firm—Wolder, Gross & Yavner

[57] ABSTRACT

The present invention relates to a new mutant strain induced from a wild strain of the genus Escherichia, which is active upon a γ-glutamyl-L-cystein synthesizing enzyme system and capable of releasing γ-glutamyl-L-cystein synthetase from inhibition by glutathione.

It preferably is *Escherichia coli* RC 912 (FERM-BP No. 47). The present invention also contemplates the preparation of glutathione by (1) culturing the foregoing strain in a culture medium' or (2) culturing said strain to first accumulate a γ-glutamyl-L-cystein synthesizing enzyme system, and placing the latter into contact with a substrate of L-glutamic acid, L-cysteine and glycerine to form gluthatione by enzymatic reaction.

9 Claims, No Drawings

MICROORGANISM AND ITS USE FOR THE PREPARATION OF GLUTATHIONE

This application is continuation of application Ser. No. 402,698, filed July 28, 1982, now abandoned.

The present invention relates to a new mutant strains of *Escherichia coli* and its use for the preparation of glutathione.

Glutathione is a kind of peptides, composed of L-glutamic acid, L-cysteine and glycine and is useful, for example, as a medicament for treating the liver disease, antidote and biochemical reagent. Conventionally, glutathione is prepared, for example, by extracting glutathione from the microbial cells of yeast; by placing a dried yeast having high permeability to membrane into contact with a substrate solution containing L-glutamic acid, L-cysteine and glycine; or by placing the microbial cells of yeast or coliform bacilli into contact with the substrate solution. With respect to the preparation of glutathione on an industrial scale, such known processes have however been characterized by poor yields.

The present invention is based upon the discovery that a certain mutant strain which we have induced from a wild strain of *Escherichia coli* is capable of accumulating large amounts of glutathione and an enzyme system for the synthesis of glutathione in the cultured broth.

Thus, an object of the present invention is to provide a new mutant strain of *Escherichia coli* and its use for the preparation of glutathione by culturing, said mutant strain being capable of accumulating abundant quantities of glutathione and an enzyme system for the synthesis of glutathione in the cultured broth.

According to the present invention, there is provided a new mutant strain of *Escherichia coli,* which is characterized by the mutant strain being active upon a γ-glutamyl-L-cysteine synthetising enzyme system and is capable of releasing γ-glutamyl-L-cysteine synthetase from the inhibition by glutathione.

The present invention will fully and clearly be described in the following specification.

Any and all mutant strains induced artificially or naturally from the wild strain of *Escherichia coli* may be used for the purpose of the present invention, provided that they are active upon γ-glutamyl-L-cysteine synthetase (E.C. 6.3.2.2., hereinafter referred to as GHS-I) and glutathione synthetase (E.C. 6.3.2.3., hereinafter referred to as GSH-II) and able to release GSH-I from the inhibition by glutathione. However, it is preferred to use *Escherichia coli* RC912 (FERM-BP No. 47) which may be obtained, for example, in the following manner.

A wild strain of *Escherichia coli* such as *E. coli* B 355 [ATCC 23226, J. Appl. Biochem. 1, 283 (1979)] which is active upon GSH-I and GSH-II as hereinbefore defined is treated to induce a cysteine-requiring strain and a methylglyoxal-resistant strain. The induction of mutant strains may be effected in a conventional manner, for example, by using N-methyl-N'-nitro-N-nitrosoguanidine (NTG), although it is also possible to use other mutagens and/or the irradiation of ultraviolet ray if desired. After this, the treated strain is cultured by using a minimum medium containing L-cysteine $(2 \times 10^{-5}M)$ and having a composition of $K_2HPO_4$ (0.7%), $KH_2PO_4$ (0.3%), $(NH_4)_2SO_4$ (0.1%), $MgSO_4 \cdot 7H_2O$ (0.01%) and glucose (0.5%) [pH about 7.0; hereinafter referred to as DM medium] at a temperature of 30°–37° C. for 16–40 hours with shaking to obtain smaller colonies, from which a cysteine-requiring strain may be obtained and purely cultured under the same conditions. Separately, the strain after induction treatment is cultured under similar conditions by using a DM medium containing methylglyoxal $(2 \times 10^{-3}M)$ to obtain larger colonies, from which a methylglyoxal-resistant strain may be obtained. Then, the thus-obtained methylglyoxal-resistant strain is transferred to the above-mentioned DM medium containing the cysteine-requiring strain for culturing under the same conditions to obtain colonies having no halo around them, from which a mutant strain such as *E. coli* C 912 may be obtained. This strain which is deficient in the productivity of GSH-I is then treated with NTG in a similar manner to that described above to induce mutation, followed by culturing under the same conditions as described above by using a DM medium containing 8-hydroxyquinoline $(2 \times 10^{-4}M)$ to obtain colonies, from which a mutant strain having an activity upon GSH-I and GSH-II and being released from the inhibition of GSH-I by glutathione may be obtained. The thus-obtained strain has been cultured over extended period of time to confirm that the desired characteristics are stable so that the strain may be used for the purpose of the present invention.

The mutant strains thus obtained may be cultured in conventional manner by using an organic medium or synthetic medium containing suitable amounts of carbon sources, nitrogen sources, inorganic substances and various other substances which may promote the growth of the used strain and enhance the accumulation of glutathione. Examples of carbon sources include glucose, sucrose, fructose, starch, starch hydrolyzate, molasses and other hydrocarbons which may be used, for example, in an amount of 0.5–5.0%. As the nitrogen sources, it is preferred to use, for example, ammonium sulfate, ammonium phosphate, ammonium carbonate, ammonium acetate, and various other inorganic and organic compounds containing ammonium; peptone, yeast extract, corn steep liquor, casein hydrolyzate and various other organic substances containing nitrogen in an amount of 0.5–2.0%. Various inorganic substances such as potassium dihydrogen phosphate, dipotassium hydrogen phosphate, magnesium sulfate, manganese sulfate and the like may be used as inorganic substances in a preferred amount of 0.005 to 0.5%. The culturing may preferably be effected under aerobic conditions with shaking or with shaking and aeration. The culturing temperature may preferably be 25°–37° C. and the culturing time may preferably be 16–40 hours. In this manner, it is possible to accumulate a large amount of glutathione in the microbial cells.

After completion of the culturing, the glutathione accumulated in the microbial cells may be extracted, for example, with water by heating to 100° C. The isolation of glutathione from the extracted solution may be effected by suitable methods, for example, by treating the extracted solution with suitable ion exchange resin which is known per se.

According to another feature of the present invention, it is possible to prepare glutathione by placing the microbial cells obtained by culturing and/or a material obtained by treating such microbial cells into contact with a substrate solution containing L-glutamic acid L-cysteine and glycine to form glutathione and recovering the same.

This teaching is based upon the discovery that the microbial cells obtained by culturing may be used as an enzyme source for formation of glutathione from L-glutamic acid, L-cysteine and glycine.

In this case, the expression "a material obtained by treating the microbial cells" denotes, for example, dried microbial cells, cell-free extract obtained by ultrasonic treatment of the microbial cells, enzyme obtained by purifying such a cell-free extracted solution, as well as immobilized microbial cells or immobilized purified enzyme obtained by immobilizing the microbial cells or purified enzyme in conventional manner (e.g. by entrapping with polyacrylamide gel or carrageenan gel).

The concentrations of L-glutamic acid, L-cysteine and glycine in the substrate solution are preferably and respectively 5–50 mM, 5–50 mM and 50–100 mM. The reaction may be effected at a pH of 6–9, preferably, 7–8.5 and a temperature of 20°–50° C., preferably, 30°–37° C.

In order to promote the enzymatic reaction, it is preferred to carry out the reaction in the presence of an adenosine-5'-triphosphate (ATP) regeneration system. In this case, it is possible to use as the ATP regeneration system, the reactions caused by various enzymes present in the microorganism used for the process of the present invention, for example, acetate kinase, enzymes for glycolysis, carbamylphosphate kinase, pyruvate kinase and the like. For example, the reaction with acetokinase may with advantage be used for this purpose when 5–20 mM of magnesium ions as magnesium salt (e.g. magnesium sulfate, magnesium chloride, etc.), 2–5 mM of ATP and 5–10 mM of acetylphosphate are present in the substrate solution.

After completion of the reaction, glutathione accumulated in the reaction mixture may be isolated and purified in conventional manner, for example, by using suitable ion exchange resin. For example, the pH of the reaction solution is adjusted to 3 with sulfuric acid and the solution is passed through a cation exchange resin such as Diaion PK-228 H+ (commercially available from Mitsubishi Kasei Kogyo K.K., Tokyo) to adsorb glutathione onto the resin, from which glutathione is eluted with 0.5M ammonium hydroxide. The pH of elute is adjusted to 4.5 with sulfuric acid and passed through an anion exchange resin such as Duolite A2 $CH_3COO-$ form (commercially available from Diamond Alkali Co., U.S.A.) to adsorb glutathione onto the resin. The adsorbed glutathione is eluted with 0.5M sulfuric acid. Then, 50% ethanol is added to the eluate to give crystals of glutathione, followed by isolating the same.

The following non-limiting examples illustrate the present invention.

EXAMPLE 1

(1) Preparation of a revertant strain of *E. coli* RC912:

*E. coli* B 355 (ATCC 23226), which is active upon γ-glutamyl-L-cysteine synthetase (E.C. 6.3.2.2, hereinafter referred to as GSH-I) and glutathione synthetase (E.C. 6.3.2.3, hereinafter referred to as GSH-II), is treated to induce a cysteine-requiring strain and a methylglyoxal-resistant strain. The induction of mutant strains was effected in conventional manner by using N-methyl-N'-nitro-N-nitrosoguanidine (NTG). After this, the treated strain was cultured by using a minimum medium containing L-cysteine ($2\times10^{-5}$M) and having a composition of $K_2HPO_4$ (0.7%), $KH_2PO_4$ (0.3%), $(NH_4)_2SO_4$ (0.1%), $MgSO_4.7H_2O$ (0.01%) and glucose (0.5%) [pH about 7.0; hereinafrer referred to as DM medium] at a temperature of 37° C. for 24 hours with shaking to obtain smaller colonies, from which a cysteine-requiring strain was obtained and purely cultured under the same conditions. Separately, the strain after induction treatment was cultured under similar conditions by using a DM medium containing methylglyoxal ($2\times10^{-3}$M) to obtain larger colonies, from which a methylglyoxal-resistant strain was obtained. Then, the thus-obtained methylglyoxal-resistant strain was transferred to the above-mentioned DM medium containing the cysteine-requiring strain ($10^{-7}$ cells/ml) for culturing under the same conditions to obtain colonies having no halo around them, from which a mutant strain *E. coli* C 912 was obtained. This strain which is deficient in the productivity of GSH-I was then treated with NTG in a similar manner to that described above to induce mutation, followed by culturing under the same conditions as described above by using a DM medium containing 8-hydroxyquinoline ($2\times10^{-4}$M) to obtain colonies, from which a mutant strain having an activity upon GSH-I and GSH-II and being released from the inhibition of GSH-I by glutathione, *E. coli* RC912 (FERM-BP No. 47), was obtained.

EXAMPLE 2

A strain shown in the following Table 1 was cultured at 37° C. for 16 hours with shaking by using 2 ml of a medium having the composition of glucose (0.5%), potassium dihydrogen phosphate (0.3%), dipotassium hydrogen phosphate (0.7%), magnesium sulfate.7H$_2$O (0.01%) and ammonium sulfate (0.1%) [pH 7.0]. After completion of culturing, the cultured broths were centrifuged (8000 r.p.m./10 min.) to collect the microbial cells which were washed with a 0.85% physiological solution of sodium chloride and extracted with hot water (1 ml; 100° C.). The amount of glutathione in the extracted solution was measured to determine the glutathione accumulated by μmole per 1 gram of the microbial wet cells. The results are shown in Table 1.

TABLE 1

| Strain | Accumulated glutathione (μmole/1 g of wet cells) |
|---|---|
| *Escherichia coli* RC912 of the present invention (FERM-BP No. 47) | 2.8 |
| *Escherichia coli* B 355 (wild strain) | 1.8 |

EXAMPLE 3

The culturing and the collection of the microbial cells were effected in a similar manner to that described in Example 2 and the ultrasonic treatment (90 KHz/5 min.) of the microbial cells was carried out to obtain a cell-free extracted solution, of which 0.05 ml was then added to a 50 mM tris-buffer solution (pH 7.5; 9.95 ml) containing L-glutamic acid (25 mM), L-cysteine (25 mM), glycine (50 mM), magnesium chloride (10 mM), acetylphosphate (10 mM) and ATP (5 mM) to effect the enzymatic reaction at 37° C. for one hour. After completion of the reaction, the amount of glutathione formed in the reaction solution was measured to determine the accumulated glutathione per one mg of protein. The results are shown in the following Table 2.

TABLE 2

| Strain | Accumulated glutathione (μmole/1 mg of protein) |
|---|---|
| *Escherichia coli* RC912 | 0.54 |

TABLE 2-continued

| Strain | Accumulated glutathione (μmole/1 mg of protein) |
|---|---|
| of the present invention (FERM-BP No. 47) | |
| *Escherichia coli* B 355 (wild strain) | 0.11 |

We claim:

1. A biologically pure culture of mutant strain *Escherichia coli* RC 912 (FERM-BP 47) which produces γ-glutamyl-L-cysteine synthetase which is not inhibited by glutathione and glutathione synthetase, and is thereby capable of producing glutathione.

2. A process for the preparation of glutathione which comprises culturing a mutant strain *Escherichia coli* RC 912 (FERM-BP 47) in a medium to accumulate glutathione in the cultured broth, and recovering the resultant glutathione therefrom.

3. The process of claim 2 wherein glutathione is recovered by aqueous extraction of the microbial cells.

4. The process of claim 2 wherein culturing is effected at a pH of from 6 to 9 and at a temperature of 25° to 37° C. for 16 to 40 hours under aerobic conditions.

5. The process of claim 2 wherein said mutant strain is cultured to produce an enzyme system comprising γ-glutamyl-L-cysteine synthetase and glutathione synthetase which produces glutathione.

6. The process of claim 5 wherein the enzyme system is carried by a carrier selected from the group consisting of microbial cells separated from the cultured broth and a cell-free extract of the cultured broth.

7. The process of claim 5 wherein the enzyme system comprises purified enzymes.

8. The process of claim 2 wherein enzymatic reaction is promoted by acetate kinase in the microbial cells in the presence of magnesium ion, adenosine-5'-triphosphate (ATP) and acetylphosphate.

9. The process of claim 2 wherein culturing is effected at a pH of 7 to 8.5 and a temperature of 30° to 37° C.

* * * * *